United States Patent [19]

Heiskanen et al.

[11] Patent Number: 5,672,628
[45] Date of Patent: Sep. 30, 1997

[54] METHOD FOR CONTROLLING A PEST POPULATION

[75] Inventors: Kalevi Heiskanen, deceased, late of Imatra, Finland, Hannu J. Salminen, legal representative; Lauri Kangas, Raisio, Finland

[73] Assignee: Orion-Yhtyma Oy, Espoo, Finland

[21] Appl. No.: 549,780

[22] PCT Filed: May 11, 1994

[86] PCT No.: PCT/FI94/00187

§ 371 Date: Nov. 14, 1995

§ 102(e) Date: Nov. 14, 1995

[87] PCT Pub. No.: WO94/26105

PCT Pub. Date: Nov. 24, 1994

[30] Foreign Application Priority Data

May 14, 1993 [FI] Finland ................................. 932220

[51] Int. Cl.⁶ ........................................................ A61K 31/135
[52] U.S. Cl. ..................................................................... 514/648
[58] Field of Search ........................................................ 514/648

[56] References Cited

U.S. PATENT DOCUMENTS 3,293,263 12/1966 Lednicer et al. .................. 260/326.5
3,419,661 12/1968 Elder ........................................ 424/243
3,480,679 11/1969 Lednicer et al. ...................... 260/609
5,135,744 8/1992 Alexander et al. .................. 424/78.17

FOREIGN PATENT DOCUMENTS 0 347 227 12/1989 European Pat. Off. .
1565334 5/1969 France .
2641943 7/1990 France .
WO 93/07749 4/1993 WIPO .

OTHER PUBLICATIONS

"Allgemeine und spezielle Pharmakologie und Toxikologie", Dr. Wolfgang Forth et al., 1988 Wissenschaftsverlag, Mannheim, Germany, pp. 416 and 417.

*CRC Handbook of Hormones, Vitamins and Radiopaques*, 1989, CRC Press, Inc., Boca Raton, Florida, U.S.A., Dr. Matthew Verderame, editor, pp. 75–84.

"Techniques for the Evaluation of Potential Rabbit (Oryctolagus cuniculus) chemosterilants", *Chemical Abstracts*, vol. 87, No. 15, Oct. 10, 1977, Columbus, Ohio, U.S.A., *ASTM Spec. Tech. Publ.*, 1977, STP 625, Test Methods Vertebr. Pest Control Manage Mater. Symp., M.E. Godfrey, Abstract No. 113094.

"Effect of Clomiphene Citrate on Ovarian and Oviducal Activities in an Avian Pest, the Yellow–Throated Sparrow (Petronia xanthocollis)", *Zoologische Jahrbücher*, International Journal for Zoological Sciences, G. Bhat et al., vol. 94, No. 3, 1990; pp. 371–374.

"Fertility of Female Mice Fed Coumestrol and Diethylstilbestrol", *Chemical Abstracts*, vol. 101, No. 13, Sep. 24, 1984; Colulmbus, Ohio, U.S.A., *J. Environ. Sci. Health, Part B*, E.A. Elias et al., pp. 441–451, Abstract No. 105776.

*Primary Examiner*—Phyllis G. Spivack
*Attorney, Agent, or Firm*—Burns, Doane, Swecker & Mathis, L.L.P.

[57] ABSTRACT

A population of pests, especially a population of rodents, can be controlled hormonally by means of baits that contain an orally active antiestrogen. The hormone present in the baits weakens the reproductive capacity of rodents thereby controls their population.

7 Claims, No Drawings

METHOD FOR CONTROLLING A PEST POPULATION

The invention relates to the control of pest population, in particular harmful rodent and bird populations, by using baits having hormonal action.

Pests such as rats, when present in large numbers, cause great economic and hygienic harm in different parts of the world by spoiling grain and foodstuffs or by transmitting diseases to people and animals. Attempts have previously been made to control pest populations by using, for example, traps and poison baits.

It has now been discovered that when baits containing an antiestrogen or a progestin as an active substance are distributed in a pest-infested area during the reproduction period of the pests, the numbers of young and newborn individuals decrease rapidly. The hormonal baits according to the invention are not lethal to the pests; the baits reduce the reproductive capacity of the pests and thus control their population. The active substances according to the invention are more nature-friendly than are the poisons commonly used for pest control, and they have not been noted to change the normal behaviour of the pests. Furthermore the pests do not have any aversion to baits of the invention.

Pests for which the method according to the invention is suitable include in particular rodents such as rat, hare and rabbit, and birds such as crow, pigeon, sparrow and gull.

The active substances according to the invention are orally active antiestrogens and progestins. The orally active antiestrogen according to the invention is preferably a non-steroidal antiestrogen. Especially suitable are non-steroidal antiestrogens having a triphenylethylene structure. Examples of these compounds are tamoxifen, 4-hydroxytamoxifen, 3-hydroxytamoxifen, toremifene, N-demethyltoremifene, 4-hydroxytoremifene and clomiphene. Of progestins, progesterone can in particular be mentioned.

It has been observed that in a rodent, such as a rat, an antiestrogen very effectively prevents the embedding of the ovum. Thus an antiestrogen reduces the reproductive capacity of rodents. Bird populations can be controlled effectively with a progestin, which prevents fertilization and thereby the development of eggs into young ones. It has also been observed that progestin prevents the reproduction of rodents, and so progestin and antiestrogen can be used either alternatively or together for rodent population control.

The invention includes a method for controlling a pest population comprising administering an antiestrogen or a progestin to pests in an amount which controls their reproduction. Especially the invention includes a method for controlling a pest population in a geographical area comprising distributing a composition containing an orally active antiestrogen or progestin mixed with an edible carrier in the area. The invention also includes new bait compositions useful for controlling a pest population.

The baits according to the invention comprise an antiestrogen or a progestin mixed with an edible carrier such baits being palatable to the pest. The edible carrier means here any non-toxic substance palatable to the pest. The edible carrier may be, for example, a foodstuff or a feed. Especially suitable carriers include grain products, pieces of bread, flours, oils such as vegetable oils or fish oils, sugar, and various mixtures of these. The active substance and the edible carrier are mixed using known methods and the resulting bait compositions are distributed in the pest-infested area. The active substance according to the invention is preferably dissolved in a food oil before being mixed with the carrier. Preferred baits for rats are cakes made of wheat flour, water and food oil, the active substance being dissolved in the food oil. The bait cakes are preferably moistened with codliver oil to improve their palatability. The finished baits are distributed in the pest-infested area, preferably daily throughout the reproductive period of the pest. The baiting period preferably last at least one natural life span of the pest. For rats the baiting period is typically 1–2 years. A suitable amount of the active substance in a bait is about 0.02–1.0 mg, preferably about 0.1–0.5 mg, per one gram of dry bait. In a rat, a dose of about 0.5 mg of the active substance suffices to inhibit the reproduction of the female. No aversion to such baits by rats has been observed. When the baits according to the invention are distributed in the rat-infested area, such as dumps, in amount of about 350 baits/day each bait containing about 0.5 mg antiestrogen, the number of young rats decrease effectively in about 2 months.

Baits can also be distributed in a pest-infested area in specific bait houses, from which the pest animals learn to come to fetch hormone baits. Bait houses can be used both at waste dumps and in population centers. Thus the baits will remain dry and the individuals in the pest population will find hormone-containing baits daily. For birds such bird houses are needed only just before the mating season.

The invention is further illustrated by the following Examples.

EXAMPLE 1

From wheat flour, water and food oil, cakes weighing approx. 2 g and containing tamoxifen citrate about 0.5 mg were prepared. The tamoxifen citrate was dissolved in the food oil used. Finished baits were placed at a dump, the rat population of which was counted before the beginning of the experiment and several times during the experiment. Special attention was paid to the number of small (young and newborn) rats. Corresponding but hormone-free baits were placed at another dump, and counting was done as above. Baits were distributed for 2 months at a rate of approx. 350 baits/day at each dump. In the rat population which was administered the hormone, young rats disappeared almost entirely within 2 months, whereas the rats which had received hormone-free baits reproduced strongly and the number of small rats increased. The experiment shows that by using antiestrogen baits a rodent population can be controlled effectively in its natural environment.

EXAMPLE 2

Progesterone or tamoxifen nitrate was mixed with chicken feed at 200 mg per 2 kg of the feed. In chickens which had received tamoxifen, 26 out of 32 eggs were fertilized. In the chickens which received progesterone, only 4 out of 35 eggs were fertilized. The experiment shows that progesterone baits inhibit effectively the reproduction of a bird population, whereas tamoxifen baits are less effective.

We claim:

1. A method for controlling a rodent population comprising applying to an environment containing a rodent population which is to be controlled, a composition which inhibits the reproductive capacity of said rodent population, wherein said composition comprises (i) an effective amount of an orally active non-steroidal antiestrogen compound which comprises a triphenylethylene structure and (ii) an edible carrier material.

2. The method of claim 1, wherein said antiestrogen is selected from the group consisting of tamoxifen, 4-hydroxytamoxifen, 3-hydroxytamoxifen, toremifene, N-demethyltoremifene, hydroxytoremifene, and clomiphene.

3. The method of claim 1, wherein said composition comprises an orally active non-steroidal antiestrogen compound having a triphenylethylene structure which is capable of being dissolved in an oil carrier.

4. The method of claim 3, wherein said composition comprises flour, water and oil.

5. The method of claim 1, wherein the amount of said antiestrogen compound contained in said composition ranges from about 0.02 to 1.0 milligrams per gram of said composition.

6. The method of claim 1, wherein said antiestrogen compound is present in an amount ranging from about 0.1 to 0.5 milligram per gram of said composition.

7. The method of claim 1, wherein the rodent population to be controlled is a rat population.

* * * * *